United States Patent [19]
Bergamasco et al.

[11] Patent Number: 5,715,834
[45] Date of Patent: Feb. 10, 1998

[54] DEVICE FOR MONITORING THE CONFIGURATION OF A DISTAL PHYSIOLOGICAL UNIT FOR USE, IN PARTICULAR, AS AN ADVANCED INTERFACE FOR MACHINE AND COMPUTERS

[75] Inventors: Massimo Bergamasco, Agrano di Omegna; Sandro Scattareggia Marchese, Pisa; Fabio Salsedo, Latina; Gianluca Parrini, Cascina, all of Italy

[73] Assignee: Scuola Superiore Di Studi Universitari & Di Perfezionamento S. Anna, Pisa, Italy

[21] Appl. No.: 428,217
[22] PCT Filed: May 16, 1995
[86] PCT No.: PCT/EP93/03238
   § 371 Date: Aug. 7, 1995
   § 102(e) Date: Aug. 7, 1995
[87] PCT Pub. No.: WO94/12925
   PCT Pub. Date: Jun. 9, 1994

[30] Foreign Application Priority Data
Nov. 20, 1992 [IT] Italy .................. TO92A0941
[51] Int. Cl.⁶ .................................................. A61B 5/10
[52] U.S. Cl. .................................................. 128/782
[58] Field of Search .................... 128/774, 782

[56] References Cited
U.S. PATENT DOCUMENTS

| | | |
|---|---|---|
| 3,258,007 | 6/1966 | Karpovich et al. |
| 4,414,537 | 11/1983 | Grimes ............... 340/365 R |
| 4,436,099 | 3/1984 | Raftopoulos ........... 128/782 |
| 4,542,291 | 9/1985 | Zimmerman .......... 250/231 R |
| 4,665,928 | 5/1987 | Linial et al. ............. 128/782 |
| 5,027,688 | 7/1991 | Suzuki et al. ........... 128/782 |
| 5,280,265 | 1/1994 | Kramer et al. ........... 338/210 |

FOREIGN PATENT DOCUMENTS

| | | |
|---|---|---|
| 0507355 | 10/1992 | European Pat. Off. |
| WO9000879 | 2/1990 | WIPO |
| WO9215247 | 9/1992 | WIPO |

*Primary Examiner*—Max Hindenburg
*Attorney, Agent, or Firm*—Sughrue, Mion, Zinn, Macpeak & Seas, PLLC

[57] ABSTRACT

A device for monitoring the configuration of a distal physiological unit comprises first position sensors for detecting quantities relating to the relative positions of a digit of an extremity of a limb and to the adduction-abduction of the digit. The device also comprises second position sensors for detecting quantities relating to the pronation-supination position of a distal portion of the limb, to the flexion-extension position of the wrist and to the adduction-abduction position of the wrist. The device comprises a glove structure bearing the fist sensors and an exoskeleton structure bearing the second sensors.

12 Claims, 4 Drawing Sheets

DEVICE FOR MONITORING THE CONFIGURATION OF A DISTAL PHYSIOLOGICAL UNIT FOR USE, IN PARTICULAR, AS AN ADVANCED INTERFACE FOR MACHINE AND COMPUTERS

BACKGROUND OF THE INVENTION

The present invention relates to a device for monitoring the configuration of a distal physiological unit comprising an extremity of a limb, the extremity being connected, by means of a wrist, to a respective distal portion of the limb and comprising at least one digit made up of phalanges.

The device may be used, in particular, to allow more natural interaction between man and informatics systems (computers and the like). In the course of the development of the art, interaction between machines and users has always been a crucial problem. With the advent of computers and their development, interaction devices have gradually been improved, permitting the production of ever more sophisticated programs in which human intervention has, to an ever greater extent, taken the form of a dialogue with the machine rather than remaining limited to programming functions and to the preliminary preparation of the input data and the subsequent analysis of the data output by the computer. In spite of this, a large part of the work of translating the data destined for the machine into a form which it can understand is still the responsibility of the user who, up to now, has had to learn and become skilled in the use of data-input devices which, although varied and of different types (keyboards, optical pens, mice, etc.), somehow limit and schematize the expressive forms by which interaction with the rest of the outside world generally and habitually take place.

In recent years a tendency to break down this technological and psychological barrier has emerged, particularly as a result of the advent of programs which reproduce events and situations pertaining to the interaction of man with the outside world, both for the purposes of training (for example, flight or war simulators) and design (of industrial products or processes, of architectural and urban environments) and even recreational, educational and humanitarian purposes (games, study programs, communication systems for the disabled), and for advanced automation applications, for example, for controlling robots working in areas which are inaccessible or dangerous to man.

All the aforementioned applications, which are given by way of non-limiting example, will be referred to generally below as "virtual-reality" applications.

Considerable efforts have recently been concentrated on the identification of interface devices which can transmit to a machine signals indicative of the configuration of the user's hand and, in particular, of the fingers of a hand.

European patent application No. 211984 describes an interface device comprising a glove which is intended to be fitted on the operator's hand and bears a plurality of optical sensors which can detect the flexion of the fingers. The position of the operator's hand in space is detected by means of a system comprising reception sensors which are steady relative to the glove and which reconstruct the position of the glove by virtue of signals sent by a transmitter carried by the glove as it moves. Another device for monitoring the configuration of the hand is described in international patent application WO90/00879 in which an exoskeleton comprising a plurality of lever arms articulated to each other and coupled to Hall-effect sensors is fixed to the phalanges of the fingers.

However, all the known systems have the disadvantage that they supply incomplete and inadequate data and are hence limited to very specific applications relating to the position and the configuration of an operator's hand. In fact, it has been found that incomplete monitoring of the positions of the fingers of the hand, even with the additional monitoring of its absolute position in space, is not satisfactory in more advanced virtual-reality applications which involve the identification of complex movements performed by the human user, for example, during the normal manipulation and gripping of objects.

For example, although the solution illustrated in European application No. 211984 is structurally simple, it has the disadvantages that it provides incomplete monitoring of the configuration of the hand and non-linear and imprecise output signals. On the other hand, the solution of application WO90/00879 enables precise signals to be obtained but to the detriment of simplicity and lightness of construction and convenience of use.

SUMMARY OF THE INVENTION

The object of the present invention is to provide a device of the type indicated above which overcomes the aforementioned problems.

Another object of the present invention is to provide an interface device which is cheap and easy to produce and which at the same time ensures precise and reliable monitoring of the configuration of the distal physiological unit.

In order to achieve these objects, the subject of the present invention is a device of the type indicated above, characterized in that it comprises, in combination:

a) first position sensor means for detecting quantities relating to positions selected from the group constituted by:
   the relative positions of the phalanges of the at least one digit, and
   the adduction-abduction position of the at least one digit;

b) second position sensor means for detecting quantities relating positions selected from the group constituted by:
   the pronation-supination position of the distal portion of the limb,
   the flexion-extension position of the wrist, and
   the adduction-abduction position of the wrist.

The device according to the present invention can monitor all the movements of the distal physiological unit which are necessary and sufficient to reconstruct, for example, complete gripping and manipulation procedures in virtual-reality or robot-control applications.

The device is constituted essentially by two main components:
   a glove structure equipped with the first sensor means, and
   an exoskeleton equipped with the second sensor means.

The glove structure is characterized in that the relative positions of the phalanges of the digits are monitored by sensor means comprising one or more flexible plates which are connected to the digits and can bend resiliently as a result of the flexion of the digits.

The present invention enables signals indicative of the movements and positions of the distal physiological unit to be transmitted with considerable precision whilst remaining of very simple construction. Moreover, it permits natural movements by the user since the bulk and weight of the device as a whole are very low. A further advantage is that it is possible to produce a device which can be adapted quickly and easily to fit a plurality of operators of different constitutions, within a wide range of anthropometric sizes.

BRIEF DESCRIPTION OF THE DRAWINGS

Further characteristics and advantages will become clear from the following description of a preferred embodiment, given with reference to the appended drawings, provided purely by way of non-limiting example, in which.

DETAILED DESCRIPTION OF THE INVENTION

Figure 1:
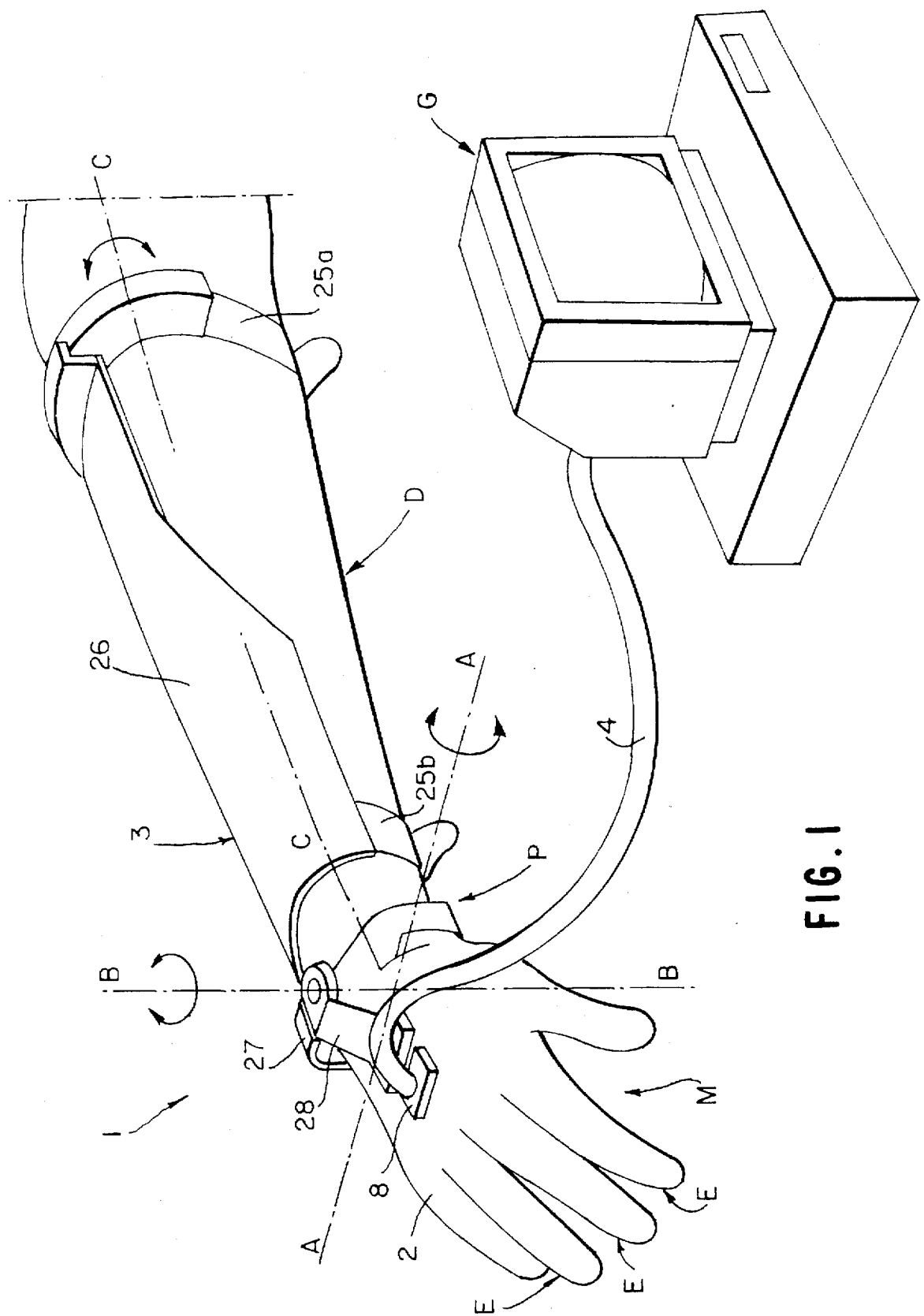
FIG. 1 is a schematic, perspective view of the device according to the present invention.
Figure 2:
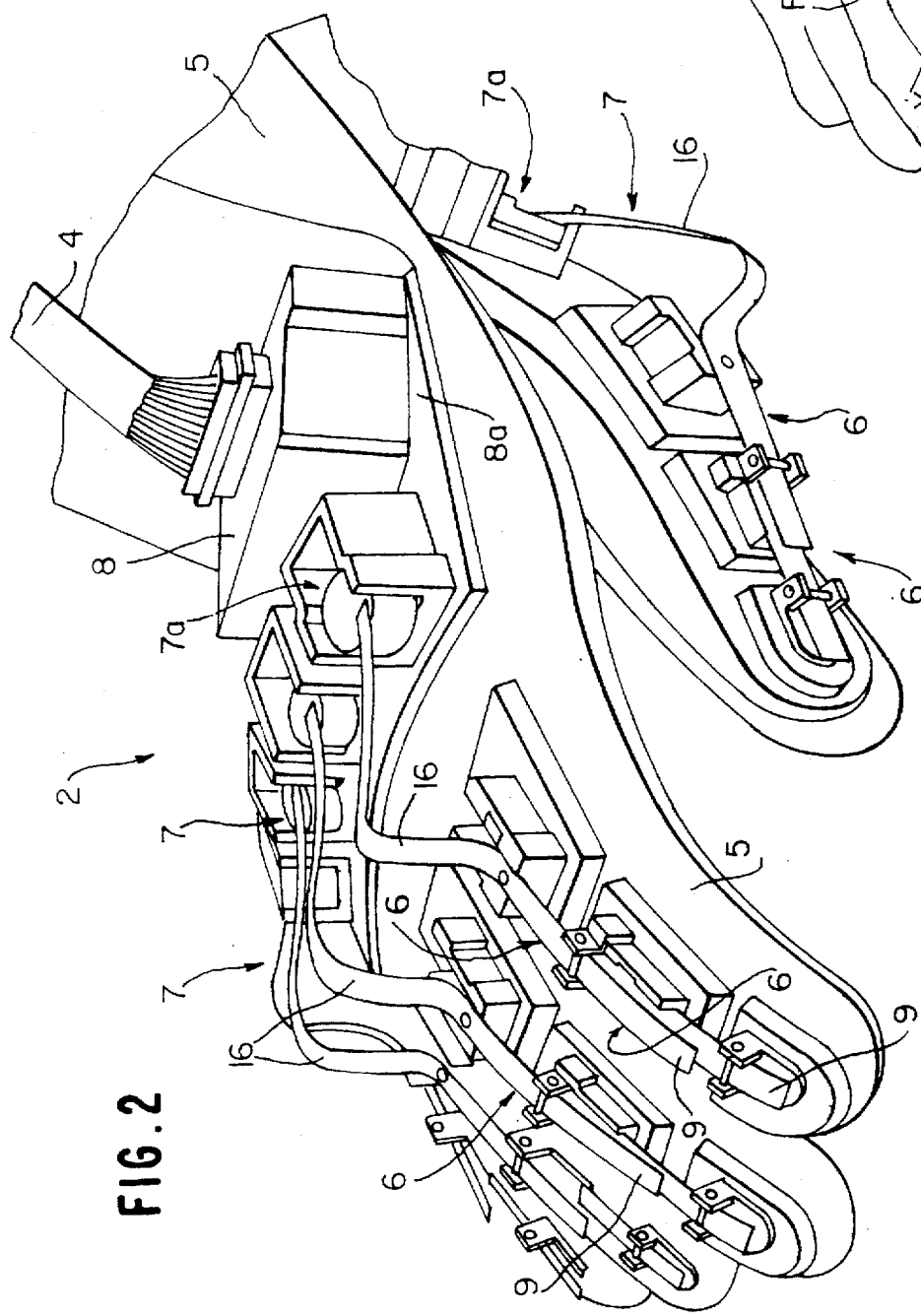
FIG. 2 is a perspective view showing the sensor-bearing glove, on an enlarged scale.

With reference now to FIG. 1, a device for detecting the configuration of a distal physiological unit comprising a hand M connected by means of a wrist P to a forearm D is generally indicated 1. The device 1 comprises a sensor-bearing glove 2 (see FIG. 2) and an exoskeleton 3 which partially covers the forearm D. The device illustrated enables the relative positions of the phalanges F of the fingers E of the hand M, the flexion-extension positions (pivoting about the axis A—A) and the adduction positions (pivoting about the axis B—B) of the wrist P, and the pronation-supination positions (rotation about the axis C—C) of the forearm D to be monitored. The device 1 is connected electrically, by means of the electrical cable 4, to a computer G which processes and controls the position data in accordance with the program running therein.

Figure 3:
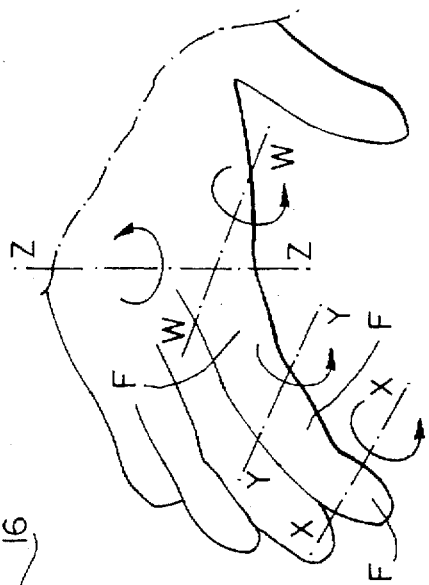
FIG. 3 is a schematic representation of the movements monitored by the glove of FIG. 2.

The sensor-bearing glove 2 is constituted by a substrate structure 5 which is intended to be fitted at least partially on the operator's hand M, and to which sensors 6 for detecting the positions of the phalanges F of the fingers and combined sensors 7, 7a for detecting flexion and abduction-adduction movements of the metacarpal-phalanx joint of each finger E are fixed. On the substrate 5, on the back of the hand M, there is a stiffened plate 8a which houses a push-in connector 8 connected to the cable 4. The sensors 6 can detect the pivoting of the phalanges F of each finger E about the axes X—X and Y—Y (see FIG. 3), whilst the sensors 7, 7a can detect pivoting about the axes W—W and Z—Z, respectively.

Figure 4:
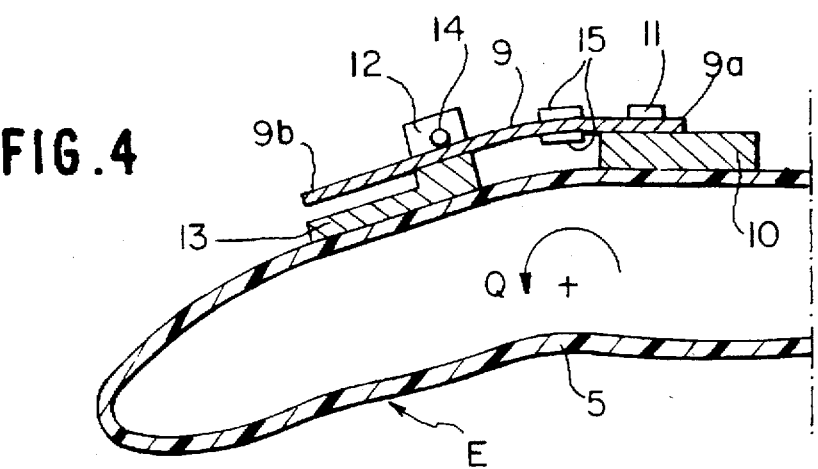
FIG. 4 is a longitudinal section of a finger of the glove of FIG. 2, on an enlarged scale, showing one of the sensors associated therewith.

As shown in FIG. 4, each of the flexion sensors 6 comprises a flexible plate 9 which is elongate along the finger E and an end 9a of which is fixed to a small support plate 10 by means of a screw 11. The plate 10 is glued or, in any case, fixed to the substrate structure 5 of the glove on the back region of a phalanx F to which the adjacent phalanx, which can be flexed in the sense indicated by the arrow Q, is articulated. The opposite end 9b of the plate 9 to its end 9a is flanked by two flanges 12 of a reaction element 13 which is also fixed to the substrate 5 on the back region of the adjacent phalanx F. A pin 14, mounted transverse the plate 9 in holes formed in the flanges 12, presses against the upper surface of the plate 9, opposing its tendency to move rectilinearly and causing it to bend as a result of relative pivoting of the phalanges in accordance with the arrow Q. Two extensometers 15 are fixed opposite the two surfaces of the plate 9 in a position intermediate the small plate 10 and the reaction element 13 and are connected electrically to the connector 8.

Figure 5:
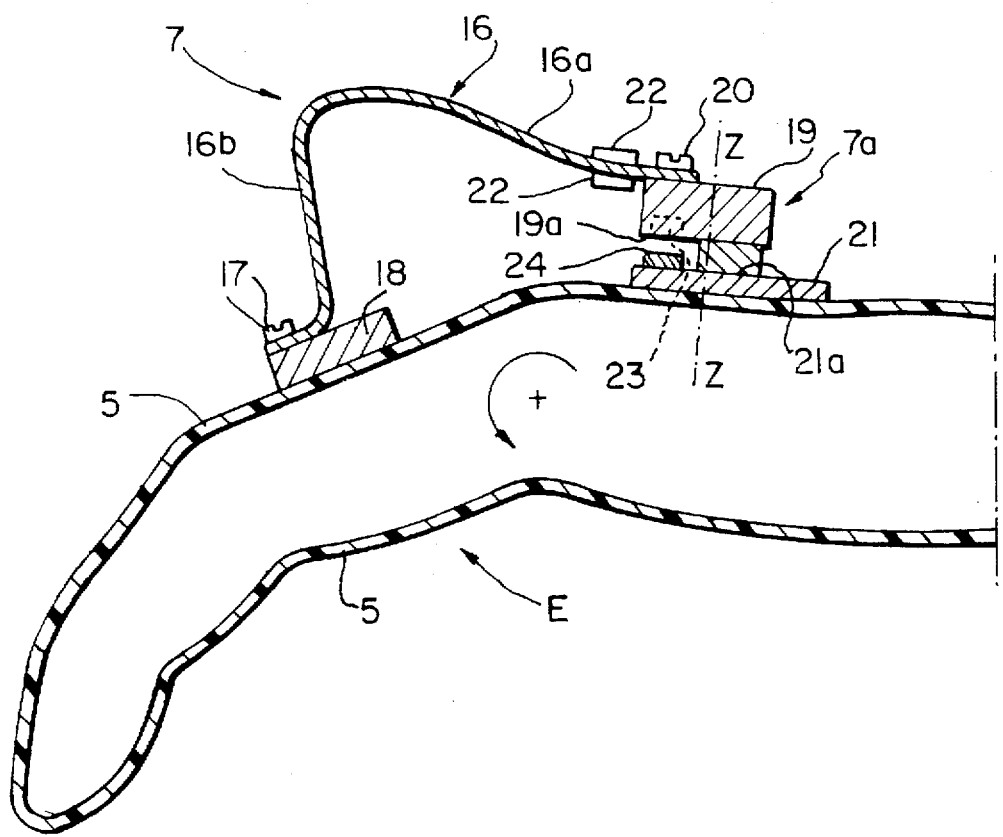
FIG. 5 is a longitudinal section similar to FIG. 4, showing another sensor carried by the glove of FIG. 2.

The generic flexion sensor 7 shown in detail in FIG. 5 is combined with the adduction-abduction sensor 7a and comprises a substantially step-shaped flexible plate 16 having a first, slightly arcuate portion 16a and a second portion 16b which is substantially perpendicular to the proximal phalanx of the finger E and is connected, by means of a screw 17, to a small traction plate 18 fixed to the substrate 5. The plate portion 16a is fixed eccentrically, by means of a screw 20, to a drum 19 which forms part of the sensor 7a and can rotate about the axis Z—Z on a support plate 21 which is also fixed to the substrate 5 on the back metacarpal region of the hand. Two extensometers 22 are fixed opposite the two surfaces of the portion 16a of the plate 16 in the same way as the extensometers 15. Two recesses formed in the lower wall 19a of the drum 19 are disposed at the same radial distance from the axis Z—Z and a certain angular distance apart and house respective magnets 23 facing the upper surface 21a of the plate 21, on which a Hall-effect sensor 24 is mounted. The magnets 23 display opposite polarities towards the surface 21a and, when the sensor 7a is in the rest condition, are equidistant from and on opposite sides of a vertical plane passing through the centreline of the Hall sensor 24. The sensor-bearing glove 2 may conveniently be covered by an outer covering sheath.

Figure 6:
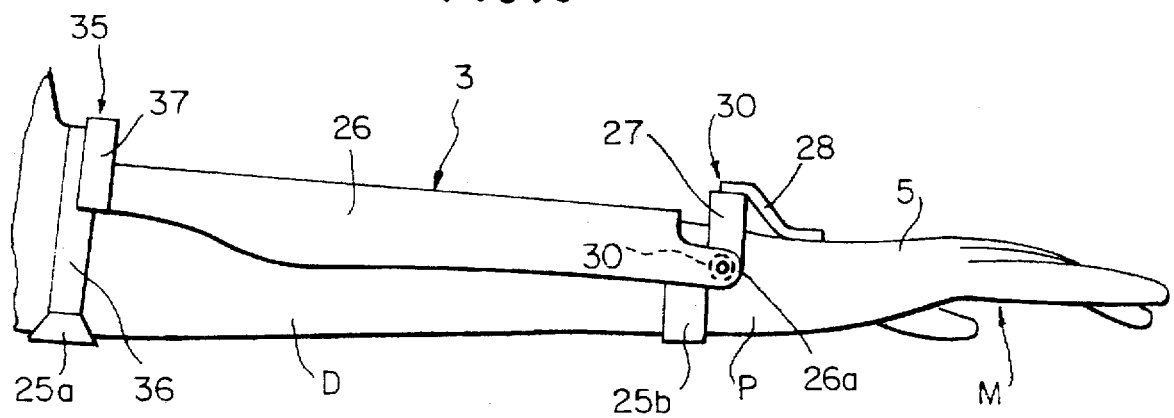
FIG. 6 is a side view of the exoskeleton structure of the device according to the present invention, in the fitted, operative condition.
Figure 7:
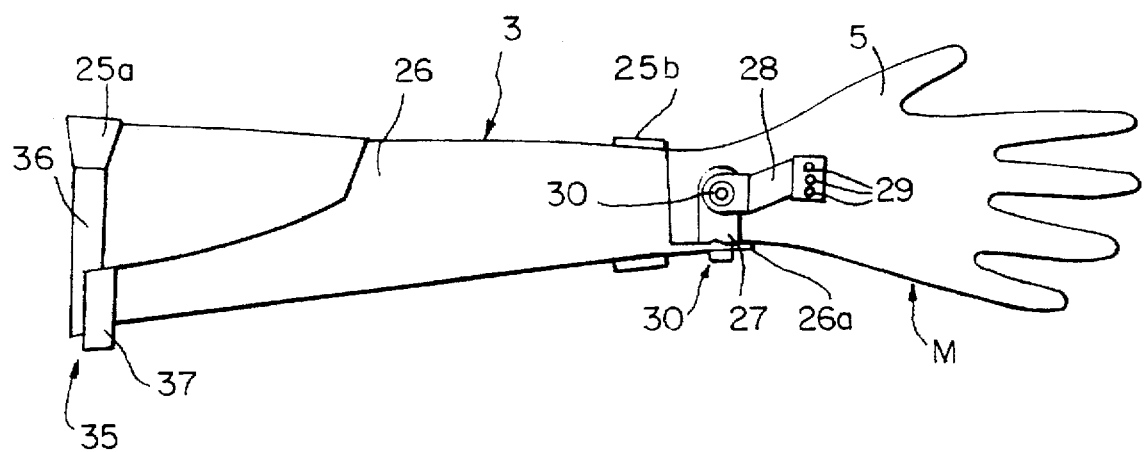
FIG. 7 is a view of the exoskeleton structure of FIG. 6, from above.

With reference now to FIGS. 6 and 7, the exoskeleton 3 is intended to be fixed to the operator's forearm D by means of two tightening straps 25a, 25b of known type near the elbow and near the wrist P, respectively. The exoskeleton 3 comprises an elongate shell-like structure 26 which partially covers the forearm D and is extended by a tongue 26a beside the wrist. The tongue 26a is connected pivotably to an L-shaped bracket 27 which extends over the upper portion of the wrist P where it is connected pivotably to an S-shaped bracket 28. The bracket 28 is connected to the plate 8a of the sensor-bearing glove 2 by means of screws 29 in the back region, behind the connector 8.

Figure 8:
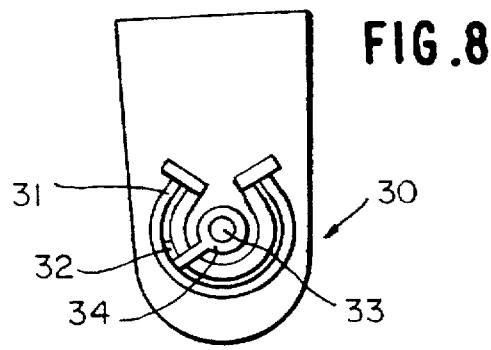
FIG. 8 is a view of a sensor used in the present invention, on an enlarged scale.

Rotation sensors 30 of the type with conductive plastics film, of which an example is shown in FIG. 8, are positioned on the pivotable connections between the tongue 26a and the bracket 27 and between the bracket 27 and the bracket 28. Each sensor 30 is constituted by an annular strip of polyamide or the like to which a track 32 of conductive material is applied. The strip 31 is fixed to one of the two pivotably-connected elements, whilst the other element, which is rotatable about a pin 33, rotates a metallized slider 34 in electrical contact with the track 32. The sensor 30 behaves like a variable resistor and is electrically connected to electrical wires (not shown in the drawing) at the ends of the track 32 and on the slider 34.

The exoskeleton portion 3 nearest the operator's elbow comprises a sensor, generally indicated 35 and also formed by conductive-film technology, for monitoring the pronation-supination of the forearm D. The sensor 35 comprises an annular track 36 which extends around most of the forearm D and a slider 37 which is carried by the shell-like structure 26 and is connected for sliding along the track 36 in electrical contact therewith during the rotary movement of the forearm D about its principal axis C—C (see FIG. 1).

On the internal surface of the shell-like element 26 there is a layer of memory-provided elastomer which enables the exoskeleton 3 to be adapted easily to fit the operator's forearm D, at the same time enabling it to be remodelled and used to fit the morphological structures of different operators.

The various sensors 6, 7, 24, 30, 35 included in the device 1 are connected, by means of the cable 4, to an electronic processing unit which can provide output electrical values the magnitudes of which are representative of the values of the physical quantities detected by the sensors.

When the device 1 is in operation, for example, in combination with the computer G, flexion or extension of the operator's fingers E brings about corresponding bending or extension of the plates 9 and 16. The electrical resistances of the extensometers 15, 22 which are glued to the surfaces of the plates and are electrically connected in a bridge arrangement thus change according to the position adopted by phalanges F of the hand M.

Moreover, as a result of the adduction-abduction movement of the fingers E, the plates 16 rotate the drums 19, causing a change in the magnetic fields detected by the Hall-effect sensors 14 and produced by the magnets 23 fixed to the drums 19. Moreover, the pivoting of the wrist P about the axes A—A, B—B and the rotation of the forearm D about the axis C—C bring about changes in the resistances of the conductive-film sensors 30, 35. The electrical magnitudes supplied by the electronic processing unit, which depend on the physical quantities detected, are processed simultaneously or with a multiplexer by acquisition systems which may conveniently be located in the computer G, thus contributing to the overall lightness of the device 1.

The sensors with which the sensor-bearing glove 2 is provided enable very great precision to be achieved in the determination of the positions of the phalanges of the fingers. Moreover, by virtue of the opposed arrangement of the extensometers 15, 22, the sensors are self-compensating and are not influenced by purely tensile or compressive deformations of the places 9, 16 due, for example, to the friction between the plates 9 and the pins 14 or to thermal variations to which the material of the plates may be subject.

The substrate of the glove 5 may also be formed in a manner such as to have a comfortable palmar surface made of materials which are soft to the touch, or may even be reduced to the essential minimum in order not to compromise the operator's sense of touch.

The device according to the present invention is not, however, limited to the details of construction and forms of embodiment described and illustrated purely by way of example. In fact variants of construction and of use may be provided for without departing from the scope of the present invention, for example, by the adaptation of the constituent elements of the device for application to a limb prothesis, in the case of a disabled operator.

What is claimed is:

1. A device for monitoring the position of a physiological unit comprising a limb and an extremity (M) connected to the limb, the extremity comprising at least one digit (E) made up of phalanges (F), the device comprising:

first position sensor means (6, 7, 7a) for at least detecting quantities relating to the relative positions of the phalanges (F) of the at least one digit, wherein the first sensor means comprise one or more flexible plates (9, 16) which are connected to the at least one digit and can bend resiliently as a result of the flexion of the fingers (E); and second position sensor means (30, 35) for detecting quantities relating to:

the pronation-supination position of a distal portion (D) of the limb which is connected, by means of a wrist (P), to the extremity (M) of the limb;

the flexion-extension position of the wrist (P); and the adduction-abduction position of the wrist (P);

wherein said device comprises a glove structure (2) bearing the first sensor means (6, 7, 7a) and an exoskeleton structure (3) bearing the second sensor means (30, 35), the extremity and the distal portion of the limb being a hand (M) and a forearm (D), respectively; and wherein the exoskeleton structure (3) comprises:

an elongate shell-like element (26) which extends along substantially the entire length of the forearm (D), a first bracket (27) pivotally mounted on the shell-like element (26), and a second bracket (28) pivotally mounted on the first bracket (27) and connected to the glove structure (2).

2. A device according to claim 1, characterized in that said first position sensor means (6, 7, 7a) also detect quantities relating to the adduction-abduction position of the at least one digit.

3. A device according to claim 2, characterized in that the glove structure (2) comprises Hall-effect sensors (14) for detecting the adduction-abduction positions of the digits (E).

4. A device according to claim 1, characterized in that the exoskeleton structure (3) is intended to be fixed to the forearm (D) by releasable retaining means (25a, 25b).

5. A device according to claim 1, characterized in that the shell-like element (26) is rotatable about the pronation-supination axis of the forearm (D) on guide means (36) fixed to the forearm substantially at the end of the shell-like element (26) which, when fixed to the forearm (D), is furthest from the wrist (P).

6. A device according to claim 5, characterized in that the brackets (27, 28) are mounted near the wrist (P), the first bracket (27) being pivotable about the flexion-extension axis of the wrist (P), substantially perpendicular to the pronation-supination axis of the forearm (D), the second bracket (28) being pivotable about the adduction-abduction axis of the wrist (P) substantially perpendicular to the other two axes.

7. A device according to claim 6, characterized in that the second sensor means (30, 35) are mounted on the connections of the shell-like element (26) and the guide means (36), of the first bracket (27) and the shell-like element (26), and of the second bracket and the first bracket (27), respectively, and can detect the relative pivoting and rotation of the elements making up the exoskeleton (3).

8. A device according to claim 7, characterized in that at least one of the second sensor means (30, 35) comprises a conductive track (32) and a slider (34) moveable thereon, the sensor means showing an electrical resistance value which is variable according to the position of the movable slider (34) relative to the ends of the conductive track (32).

9. A device according to claim 1, characterized in that the flexible plates (9, 16) are associated with respective extensometric sensor means (15, 22) showing electrical resistance values which are variable according to the degree of bending of the plates (9, 16).

10. A sensor-bearing glove structure (2), particularly for virtual-reality applications and the like, comprising:

a substrate structure (5) disposed in said glove for fitting onto a hand (M) comprising fingers (E) made up of phalanges (F), first position sensor means (6,7) for detecting quantities relating to the relative positions of the phalanges (F), and second position sensor means (7a) for detecting quantities relating to the adduction-abduction positions of the fingers (E), wherein the first sensor means (6,7) comprise one or more flexible plates (9,16) which are connected to the fingers and can bend resiliently as a result of the flexion of the fingers (E), wherein the second position sensor means (7a) comprise at least one Hall-effect sensor (24), and wherein the second sensor means further comprises at least one drum-like element (19) which can oscillate about the adduction-abduction axis (Z—Z) of a finger (E), and magnetic means (23) which are associated with the drum-like element (19) and can rotate eccentrically relative to the axis (Z—Z) as a result of an oscillation of the drum-like element (19), the Hall-effect sensor (24) being able to detect the magnetic-field variations produced by oscillations of the magnetic means (23).

11. A sensor-bearing glove structure (2) according to claim 10, characterized in that at least one of the plates (16) is connected eccentrically to the at least one drum-like element (19) to cause it to oscillate as a result of adduction-abduction movements of a finger (E).

12. A sensor-bearing glove structure (2) according to claim 10, characterized in that the flexible plates (9, 16) are associated with respective extensometric sensor means (15, 22) having electrical resistance values which are variable according to the degree of bending of the plates (9, 16).

* * * * *